United States Patent [19]

Tokinage et al.

[11] 4,401,387
[45] Aug. 30, 1983

[54] NEPHELOMETRIC IMMUNOASSAY AND NEPHELOMETER

[75] Inventors: Daizo Tokinage; Teruaki Kobayashi; Mitsuyoshi Yuasa, all of Hachioji; Michio Itoh, Tokorozawa; Kazuo Yasuda, Katsuta, all of Japan

[73] Assignee: Hitachi, Ltd., Tokyo, Japan

[21] Appl. No.: 294,055

[22] Filed: Aug. 18, 1981

Related U.S. Application Data

[63] Continuation of Ser. No. 40,205, May 18, 1979, abandoned.

[30] Foreign Application Priority Data

May 19, 1978 [JP] Japan .................. 53-58933

[51] Int. Cl.$^3$ .............. G01N 21/51; G01N 21/75; G01N 33/48
[52] U.S. Cl. .................. 356/341; 356/343; 356/442; 436/805
[58] Field of Search ............... 356/337–343, 356/39, 442, 435; 250/574; 23/230 B, 915; 435/7, 808; 424/12–13; 436/805

[56] References Cited

U.S. PATENT DOCUMENTS

| 3,714,444 | 1/1973 | Carr et al. | 356/442 |
| 4,157,871 | 6/1979 | Anderson et al. | 356/341 |
| 4,164,558 | 8/1979 | Schulthess et al. | 23/230 B |
| 4,174,952 | 11/1979 | Cannell et al. | 356/341 |
| 4,268,171 | 5/1981 | Sternberg | 356/341 |

OTHER PUBLICATIONS

Buffone et al. "Evaluation of Kinetic Light Scattering as an Approach to the Measurement of Specific Proteins with the Centrifugal Analyzer 11 Theoretical Considerations", Clin. Chem. vol. 21, #12, 1975, pp. 1735–1746.

Primary Examiner—William H. Punter
Attorney, Agent, or Firm—Antonelli, Terry & Wands

[57] ABSTRACT

A nephelometric immunoassay and a nephelometer therefore, characterized in that light is projected on a sample to-be-measured containing an antigen-antibody complex, that at least two light scattering intensities at different angles with respect to the incident light are measured, and that a true antigen concentration is discriminated by comparing the light scattering intensities.

17 Claims, 17 Drawing Figures

FIG. 6
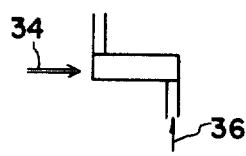
FIG. 7A   FIG. 7B
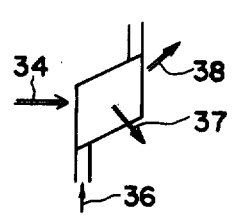 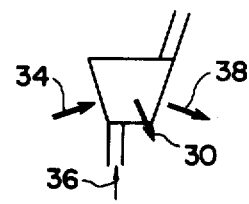
FIG. 7C   FIG. 7D   FIG. 7E
  
FIG. 7F   FIG. 7G
 

NEPHELOMETRIC IMMUNOASSAY AND NEPHELOMETER

This is a continuation of application Ser. No. 040,205, filed May 18, 1979, now abandoned.

BACKGROUND OF THE INVENTION

This invention relates to the nephelometric immunoassay which is one of immunoassays for measuring various components contained in body fluids such as blood and urine, for example, various sorts of immunoglobulins etc., and also to a nephelometer therefor.

In the nephelometric immunoassay wherein an antigen-antibody complex formed by an antigen-antibody reaction is measured by a light scattering photometer, there is a relationship as schematically shown in FIG. 1 between the light scattering intensity and the antigen concentration, and hence, two different values of antigen concentrations are obtained for one light scattering intensity. Therefore, even when the measurement is performed in a range 1 in FIG. 1 by adjusting the dilution ratio of a sample, etc., the measured sample sometimes contains an unexpectedly high concentration of antigen, and the measurement is feared to actually proceed in a range of antigen excess 2 in FIG. 1. In a priorart method, accordingly, two specimens of unequal dilution ratios are prepared and measured for each sample. It is decided by studying the proportional relation between the light scattering intensity and the dilution ratio that the specimen falls in the range 1 in FIG. 1, and the value of a correct antigen concentration is obtained. Therefore, much labor and many specimens are required for the measurement.

LIST OF PRIOR ART (37 CFR 1.56(a))

The following references are cited to show the state of the art:

Japanese Published Unexamined Patent Application No. 53-13492,

C. D. Deaton et al, "Use of Laser Nephelometry in the Measurement of Serum Proteins", Clin. Chem., Vol. 22, No. 9, 1465–1471 (1976).

SUMMARY OF THE INVENTION

An object of this invention is to provide an improved nephelometric immunoassay and an improved nephelometer.

Another object of this invention is to provide a nephelometric immunoassay and a nephelometer in which a true value can be known with a single sample concentration.

These and other objects are accomplished in such a way that light is projected on a measurement sample containing an antigen-antibody complex, that at least two light scattering intensities at different angles with respect to the incident light are measured, and that a true antigen concentration is discriminated by comparing the light scattering intensities.

BRIEF DESCRIPTION OF THE DRAWINGS

FIG. 6 is a sketch showing the shape of a cell, FIGS. 7A, 7B, 7C, 7D, 7E, 7F and 7G are sketches each showing the shape of a cell.

DETAILED DESCRIPTION OF THE PREFERRED EMBODIMENTS

Basically, this invention consists in projecting light on a sample containing an antigen-antibody complex and measuring at least two light scattering intensities at different angles with respect to the incident light. This allows for obtaining an accurate measurement even for a measurement sample containing a high concentration of antigen.

Figure 1:
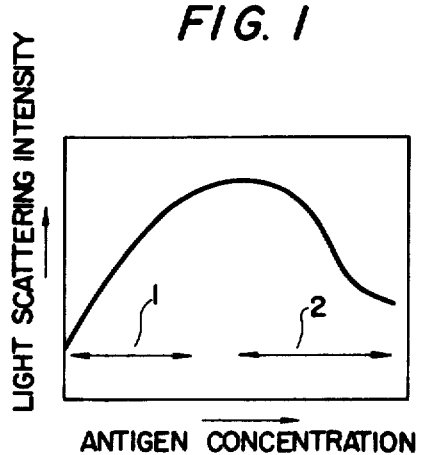
FIG. 1 is a graph for schematically explaining the measured values of an immunological measurement based on a nephelometric immunoassay.
Figure 2A:
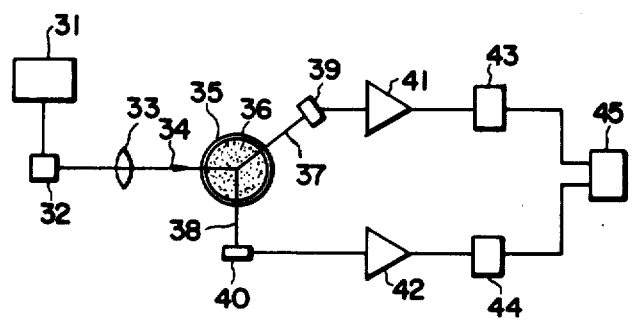
FIGS. 2A and 2B are schematic block diagrams showing an example of apparatus to which this invention is applied.

FIG. 2A is a block diagram showing an example of apparatus for performing this invention. Light 34 which is emitted from a light source 32 by an electric power supply 31 enters a sample to-be-measured 36 in a cell 35 through a lens unit 33. Scattering lights 37 and 38 at different angles with respect to the incident light 34 are respectively detected by photo detectors 39 and 40. Outputs of the respective photo detectors 39 and 40 are led to preamplifiers 41 and 42, and are amplified by amplifiers 43 and 44. A true antigen concentration is discriminated by a discriminator 45.

Figure 2B:
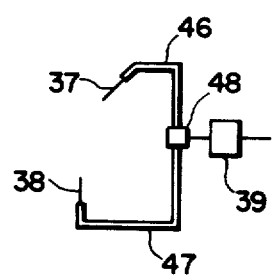

There is also a method wherein, as illustrated in FIG. 2B, the scattering lights 37 and 38 at different angles are successively guided to a photo detector with optical guides 46 and 47 and via a switch 48.

As the different angles used in accordance with the invention, angles which differ at least 5 degrees are preferable. More preferably, the difference is at least 10 degrees. A preferred example is a case where one of the scattering lights has an angle selected from a range of 30–45 degrees with respect to the incident light, for instance, an angle of 35 degrees, while the other scattering light has an angle selected from a range of 80–100 degrees with respect to the incident light, for instance, an angle of 90 degrees.

The scattering lights can be detected simultaneously or successively. That is, it is possible to measure the two scattering lights simultaneously by the use of the two detectors as illustrated in FIG. 2A. It is also possible to measure the two scattering lights successively by a method wherein only one detector is moved, the method wherein the scattering lights at the different positions are led to the single photo detector with the optical guides as illustrated in FIG. 2B, or a similar method.

Figure 3:
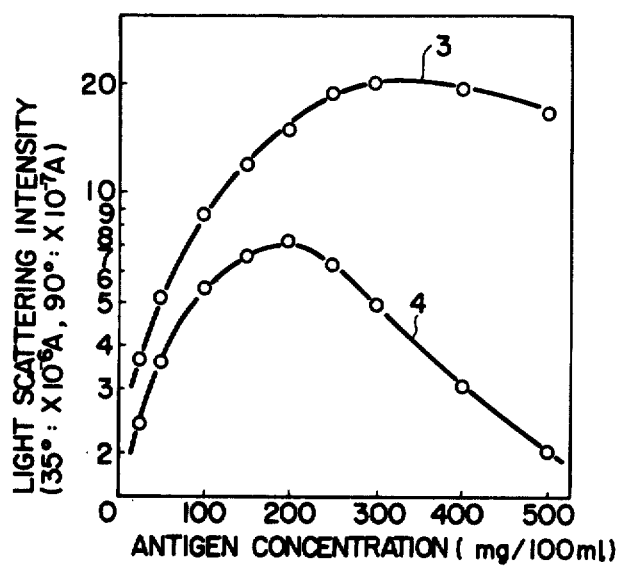
FIGS. 3 and 4 are graphs for explaining measured values according to this invention.

By way of example, two light scattering intensities at different angles are related as indicated by curves 3 and 4 in FIG. 3.

More specifically, when the measurement is carried out at light scattering measurement angles $\alpha$ and $\beta$, light scattering intensities $I_\alpha$ and $I_\beta$ are respectively expressed as functions of the antigen concentration C:

$$\left. \begin{array}{l} I_\alpha = f_\alpha(C) \\ I_\beta = f_\beta(C) \end{array} \right\} \tag{1}$$

In both the cases of the angles $\alpha$ and $\beta$, two values of antigen concentrations exist for a certain light scattering intensity. Here, let $C_{x\alpha}$, $C_{x\alpha}'$ or $C_{x\beta}$, $C_{x\beta}'$ denote antigen concentrations which are obtained from the function (1) as well as a light scattering intensity $I_{x\alpha}$ or $I_{x\beta}$ in the case of measuring a sample of an unknown concentration at the angle $\alpha$ or $\beta$, respectively. $C_{x\alpha}'$ and $C_{x\beta}'$ shall be antigen concentrations which fall within a range of antigen excess. Among these values, which of $C_{x\alpha}$ and $C_{x\alpha}'$ or which of $C_{x\beta}$ and $C_{x\beta}'$ is the true antigen concentration of the unknown sample may be discriminated.

As an example of a discriminating method, accordingly, the following discriminant may be resorted to:

$$|\ln C_{x\alpha} - \ln C_{x\beta}| < |\ln C_{x\alpha}' - \ln C_{x\beta}'| \qquad (2)$$

In a case where the discriminant (2) holds, the antigen concentration of the unknown sample is the concentration $C_{x\alpha}$ or $C_{x\beta}$ or the average value of both these concentrations. In a case where it does not hold, the antigen concentration is the concentration $C_{x\alpha}'$ or $C_{x\beta}'$ or the average value of both these concentrations.

Further, considering a case where the true concentration is intermediate between a concentration corresponding to the peak of the curve 3 in FIG. 3 and a concentration corresponding to the peak of the curve 4, a method can be adopted wherein the minimum value among four values $|\ln C_{x\alpha} - \ln C_{x\beta}|$, $|\ln C_{x\alpha}' - \ln C_{x\beta}'|$, $|\ln C_{x\alpha} - \ln C_{x\beta}'|$ and $|\ln C_{x\alpha}' - \ln C_{x\beta}|$ is found and wherein if it is, for example, $|\ln C_{x\alpha}' - \ln C_{x\beta}|$, the concentration $C_{x\alpha}'$ or $C_{x\beta}$ or the average value of these concentrations is deemed the true value.

As another method of discrimination, it is possible to set the antigen concentration C in a range which does not include the range of antigen excess, and to express the light scattering intensities $I_\alpha$ and $I_\beta$ as functions of this antigen concentration C:

$$\left. \begin{array}{l} I_\alpha = f_\alpha(C) \\ I_\beta = f_\beta(C) \end{array} \right\} \qquad (3)$$

or in approximation thereto:

$$\left. \begin{array}{l} \ln I_\alpha = A_\alpha \ln C + B_\alpha \\ \ln I_\beta = A_\beta \ln C + B_\beta \end{array} \right\} \qquad (4)$$

where $A_\alpha$, $B_\alpha$, $A_\beta$ and $B_\beta$ denote constants.

Virtual concentrations $C_{x\alpha}$ and $C_{x\beta}$ of a sample of an unknown antigen concentration are evaluated from the inverse function of the function (3) (or the equation (4)) as well as the actual measurement values $I_\alpha$ and $I_\beta$ of light scattering intensities obtained at angles $\alpha$ and $\beta$ from the unknown sample.

On the basis of what the values $C_{x\alpha}$ and $C_{x\beta}$ are, it can be determined whether or not they are actually the true concentration of the unknown sample as shown by the following example.

If a discriminant:

$$\frac{|C_{x\alpha} - C_{x\beta}|}{C_{x\alpha}} < a \qquad (5)$$

or

-continued $$\frac{|C_{x\beta} - C_{x\alpha}|}{C_{x\beta}} < a \qquad (6)$$

holds, the value $C_{x\alpha}$ or $C_{x\beta}$ is determined as the true concentration of the unknown sample. In the case where the discriminant does not hold, the unknown sample is regarded as an antigen excess sample or an unmeasurable sample, and the concentration is not determined. a in Equation (5) or (6) is a value which is to be empirically set. If the difference of the two measurement angles $\alpha$ and $\beta$ is great, the true concentration can be known even when a large value is set as a. For example, in the case of a measurement at two angles of 35° and 90°, a sufficiently accurate decision is possible even by making a about 0.1.

According to this method of discrimination, a measurement sample such as chyliferous serum can be detected as an abnormal sample.

Figure 4:
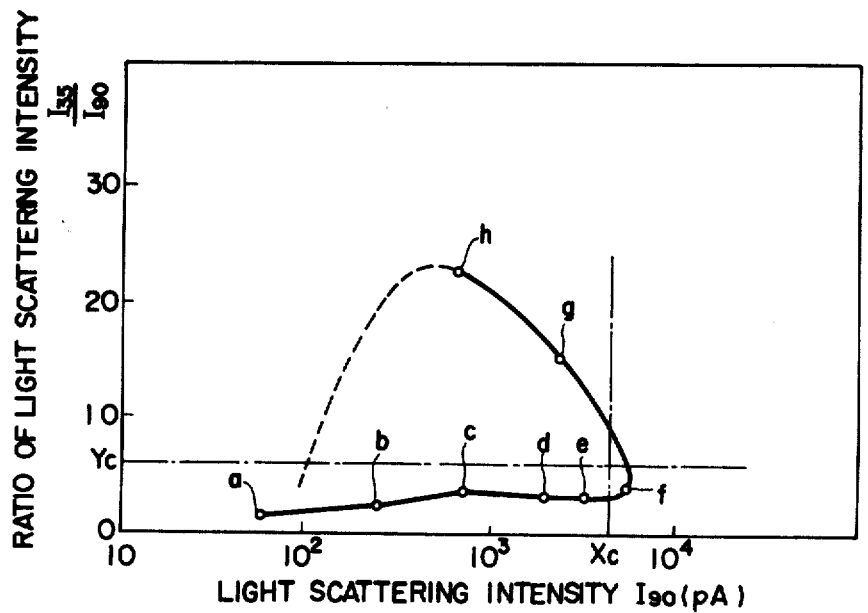

As still another method of discrimination, only a case where a light scattering intensity at a certain angle is not greater than a predetermined value and where the ratio of light scattering intensities at two angles is not greater than another predetermined value is decided to be a measurement within a normal measuring range which is not of antigen excess. The principle of this method of discrimination will now be explained in connection with a concrete example. FIG. 4 is a graph obtained in such a way that immunoglobuline G (IgG) standard samples at several concentrations were subjected to antigen-antibody reactions, that light scattering intensities in a direction of 35° and in a direction of 90° were measured, and that after subtracting an antiserum blank value, the ratio $I_{35}/I_{90}$ between the light scattering detector output in the direction of 35° and the light scattering detector output in the direction of 90° was plotted versus the light scattering detector output $I_{90}$ in the direction of 90°. As the concentrations of the standard samples become higher, the plots depict a locus $a-b-c-\ldots-h$ in FIG. 4. The plots a, b, c, d and e fall within an antibody excess region in which the normal concentration determination is possible, the plot f is a peak of the maximum light scattering intensity $I_{90}$, and the plots g and h are data in an antigen excess region. Accordingly, when a value $Y_c$ which is somewhat larger than all the actually measured values $I_{35}/I_{90}$ of the standard samples in the antibody excess region and a value $X_c$ which is somewhat smaller than the maximum actually-measured value $I_{90}$ of the standard samples are selected on the basis of the measurement of the standard samples in advance, whether or not a sample of an unknown concentration lies in the normal antibody excess region can be determined by comparing the magnitudes of the ratio $I_{35}/I_{90}$ of the unknown sample and the value $Y_c$ and by comparing the magnitudes of the value $I_{90}$ of the unknown sample and the value $X_c$.

In this case, the intensity $I_{35}$ has been taken as the numerator, and the intensity $I_{90}$ as the denominator. In the converse case where the ratio $I_{90}/I_{35}$ is employed and where the value $Y_c$ is selected to be somewhat larger than all the actually measured values $I_{90}/I_{35}$ of the standard samples in the antibody excess region in advance, it can be determined by $I_{90}/I_{35} > Y_c$ and $I_{90} < X_c$ that the unknown sample lies in the normal antibody excess region.

In FIG. 4 referred to in the above, the axis of abscissas has represented the light scattering intensity $I_{90}$.

However, a similar method of decision is possible even when the light scattering intensity $I_{35}$ is taken on the axis of abscissas. In short, the principle of the present method of decision is founded on the fact that when the ratio between light scattering intensities at two angles is plotted versus the light scattering intensity at one of the two angles, plots in an antigen excess region (g and h in the case of FIG. 4) lie at positions much spaced from plots in a normal antibody excess region. The present method of decision accordingly holds by appropriately selecting the above-defined values $X_c$ and $Y_c$ from the measurements of standard samples so that only the plots in the normal antibody excess region may fall within one of the four quadrants determined by the values $X_c$ and $Y_c$ as shown in FIG. 4.

That is, the discrimination of the true antigen concentration in this invention signifies, not only that the value of the true antigen concentration of the measurement sample is obtained, but also that even when the antigen concentration of the measurement sample is an abnormal value lying outside antigen concentrations anticipated, it is detected.

Figure 5:
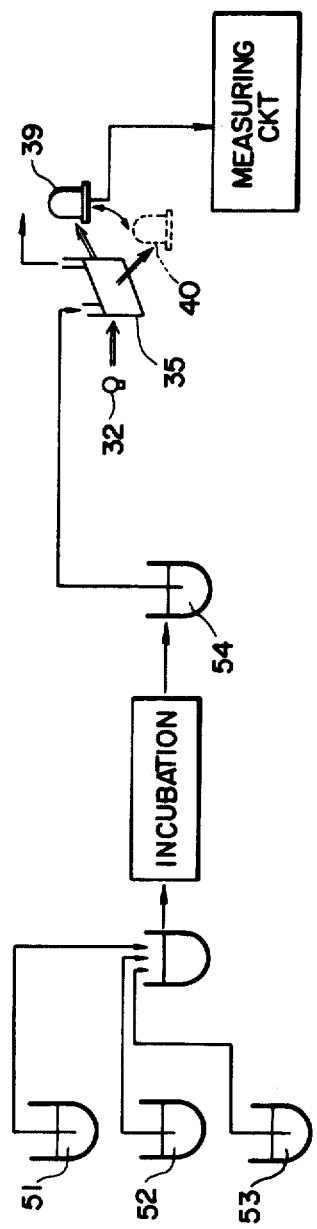
FIG. 5 is a system flow diagram for explaining this invention.

Favorably, the apparatus of this invention measures light scattering by employing a flow cell for receiving a measurement sample. When the flow cell is employed, it is facilitated to automate a process from the preparation of a sample to the measurement of scattering light as well as data processing. As illustrated in FIG. 5, a sample serum 51, a dilute solution 52 and an antiserum 53 are respectively poured in reaction vessels in suitable amounts. After stirring, they are subjected to incubation under a constant temperature for a suitable time. Subsequently, a reaction sample 54 is sucked into a scattering light-measuring cell 35, and scattering light is measured. After executing necessary processings, data are obtained. Here, the preparation and incubation of the sample may conform with the mechanism or procedure of a conventional clinical automatic analyzer. However, the scattering light-measuring cell should favorably be a novel one in accordance with the present invention. Although a method wherein the incubation and the scattering light measurement are performed with an identical disposable cell is also considered, a method wherein the incubation is performed in the vessel exclusive therefor and wherein the reaction sample is sucked into the cell (flow cell) is the simplest in mechanism and permits the expectation of a high accuracy.

Although photo detectors 39 and 40 are exemplified as moving in order to measure scattering lights at different angles, they may, of course, also be two fixed photo detectors.

FIG. 6 shows an example of a typical flow cell for a clinical automatic analyzer for reference. The feature of this cell is that it is a structure which is small in size and in which liquid flows smoothly. On the other hand, the light scattering-measuring flow cell has a structure which can view the scattering light at a certain angle with respect to an incident light beam. Moreover, in order to prevent stray light from being picked up in that case, the intersection between the incident light and the wall of the cell must not be viewed. Thus, structure of the flow cell for the clinical automatic analyzer should desirably be one having a small size and permitting the solution to flow smoothly as seen in FIG. 6. However, in a flow cell for measuring the scattering light it is difficult to adopt a structure permitting the solution to flow smoothly, due to the above restriction. Although the capacity of this cell is determined by the spreading of the incident light beam and the area of view of the scattering light, it usually becomes large as compared with the capacity of the flow cell for the clinical automatic analyzer. In the flow cell, there has been adopted a method according to which a measured solution is replaced with a solution to-be-measured by causing the latter to flow thereinto. A problem posed here is the survival of the former, that is, contamination. A polymeric buffer of high viscosity is often used in order to promote an antigen-antibody reaction in the nephelometric immunoassay. Besides the complicacy of the cell structure, this forms a cause for increasing the contamination.

FIGS. 7(A) and 7(B) show examples of scattering light-measuring hexahedral flow cells which have been fabricated by reference to the flow cell for the clinical automatic analysis. In either of these cells, when a solution is caused to flow quietly, a solution lying at a corner of the cell is not replaced completely with a solution to-be-measured. It is accordingly necessary to abruptly suck the solution and to cause the agitation of the solution in the cell. Therefore, in the case where suction and discharge ports for solutions are provided in surfaces confronting each other, the flow cell cannot be put into practical use on account of a high degree of contamination.

As the result of hydrodynamical study, it has been revealed that, in order to agitate solutions satisfactorily throughout the interior of a cell and to substitute the new solution for the old solution, suction and discharge ports for the solutions need to be provided in an identical surface of the cell or at positions close to such condition. In this case, it is desirable that the solution flowing in through the suction port strikes the opposing surface at the right angle thereto or at an angle close to the right angle. FIGS. 7C to 7G show examples of flow cells which have been fabricated by way of trial in accordance with the above study.

Examples of experimental results are listed in Table 1. In this experiment, in order to make the properties of a sample solution alike to the properties of solutions which are actually used, there was employed a solution in which 3% of polyethylene glycol having a molecular weight of about 7,500 and 0.2% of egg albumin were added to a 0.01 M phosphate buffer. The experimental temperature was set at 35° C. The viscosity of the solution at this time was 1.35 cp. The flow volume of the solution was made 2 ml, and the flow velocity about 0.8 ml/s. In Table 1, No. 1 indicates the result of a flow cell for clinical automatic analysis on which the experiment was conducted for the sake of comparison. Nos. 2 to 4 indicate the results in the case where suction and discharge ports were provided in surfaces confronting each other. Nos. 5 to 11 indicate the results of light scattering-measuring flow cells for use in this invention. As apparent from the table, when the cell capacity is made, preferably, at most 0.3 ml in the cell structure described above, the contamination can be readily made below 1%.

The cell capacity necessary for the light scattering measurement is, preferably, 0.1 ml or greater. Therefore, the preferable capacity of the flow cell is 0.1 to 0.3 ml.

The flow cell of this type has wide applications including, for example, the quantitative analysis of lipid and the measurement of bacteria as based on the light scattering measurement.

TABLE 1

| No. | Shape of Cell | Capacity of Cell (ml) | Contamination (%) |
|---|---|---|---|
| 1 | FIG. 6 | 0.25 | 5.1 |
| 2 | FIG. 7A | 0.63 | 12.7 |
| 3 | FIG. 7A | 0.59 | 11.3 |
| 4 | FIG. 7A | 0.50 | 10.0 |
| 5 | FIG. 7C | 0.61 | 3.4 |
| 6 | FIG. 7C | 0.43 | 1.1 |
| 7 | FIG. 7D | 0.63 | 5.9 |
| 8 | FIG. 7D | 0.49 | 3.3 |
| 9 | FIG. 7E | 0.44 | 2.2 |
| 10 | FIG. 7F | 0.36 | 1.4 |
| 11 | FIG. 7G | 0.32 | 1.0 |

Figure 8:
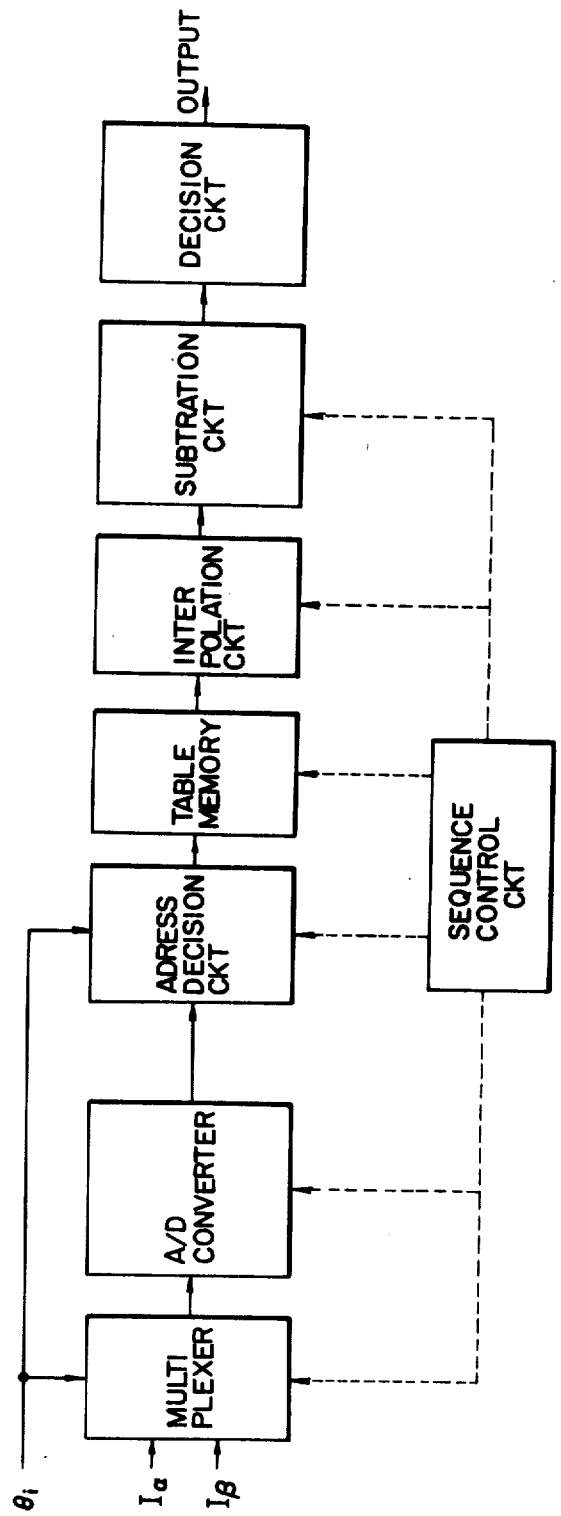
FIGS. 8, 9 and 10 are block diagrams each showing apparatus for discrimination.

FIG. 8 shows a block diagram of an example of apparatus for performing the method of discrimination of this invention. Referring to the figure, $\theta_i$ designates a signal indicative of a light scattering-measuring angle, and $I_\alpha$ and $I_\beta$ designate light scattering intensities at angles $\alpha$ and $\beta$ respectively.

The concentration values $C_{x\alpha}$, $C_{x\alpha}'$, $C_{x\beta}$ and $C_{x\beta}'$ based on the foregoing equation (1) are provided from an interpolation circuit, and the true concentration based on the discriminant (2) is provided by a decision circuit. When antigen concentrations stored in a table memory do not include ones in the range of antigen excess, the values $C_{x\alpha}$ and $C_{x\beta}$ based on Equation (3) or (4) are provided from the interpolation circuit, and the true concentration or a signal indicating that the measured sample is an abnormal sample based on discriminant (5) or (6) is provided from the decision circuit. Various circuits and the table memory in FIG. 8 are part of a micro-processor device.

Figure 9:
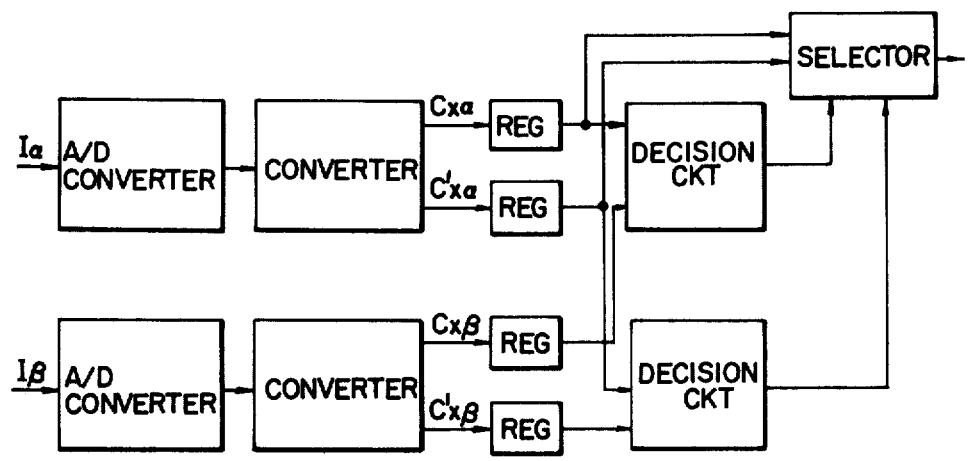

FIG. 9 is a block diagram of another example of a similar discriminator apparatus. Converters include memories which store therein two sorts of concentration values for light scattering intensities at the respective angles, and they provide the values $C_{x\alpha}$, $C_{x\alpha}'$, $C_{x\beta}$ and $C_{x\beta}'$. If the difference of the values $C_{x\alpha}$ and $C_{x\beta}$ (or $|C_{x\alpha}-C_{x\beta}|/C_{x\alpha}$) is smaller than a fixed value, a signal with the value of the particular concentration being positive is provided by a decision circuit, and the value $C_{x\alpha}$ or $C_{x\beta}$ is provided from a selector. The same applies to the case of the values $C_{x\alpha}'$ and $C_{x\beta}'$.

In a case where the memories store antigen concentrations which do not include ones in the range of antigen excess and where only the values $C_{x\alpha}$ and $C_{x\beta}$ are respectively provided from the converters, the value of the true concentration or a signal indicating that the measured sample is an abnormal sample (such as the measured sample of antigen excess and the measured sample of chyliferous serum) can be provided.

Figure 10:
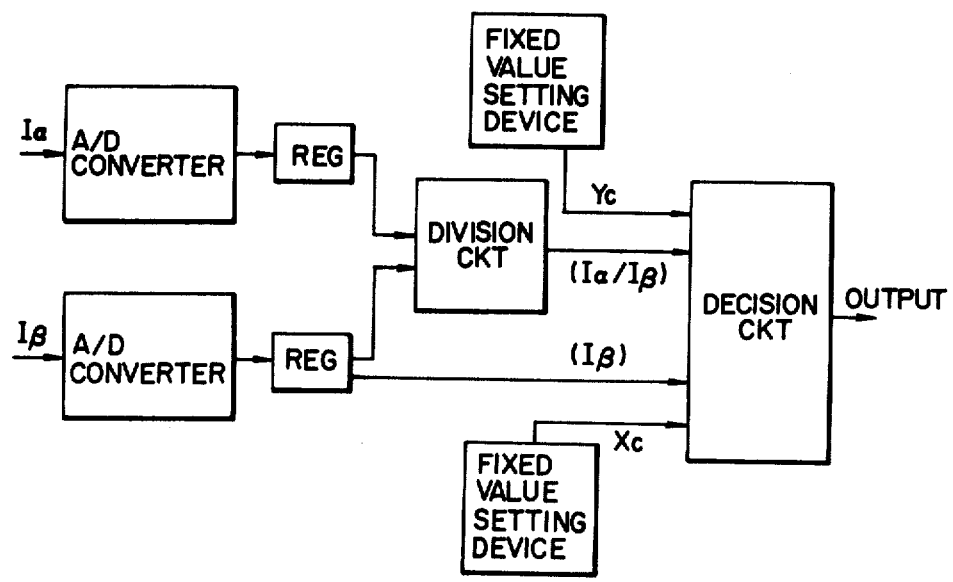

Still another discriminator apparatus is shown in FIG. 10. Signals $I_\alpha$ and $I_\beta$ of photo detectors at two angles $\alpha$ and $\beta$ are put into registers through A/D converters, and the ratio $I_\alpha/I_\beta$ is provided from a division circuit. Values $X_c$ and $Y_c$ are applied from fixed value settling devices to a decision circuit, which decides $I_\beta < X_c$ and $I_\alpha/I_\beta < Y_c$ and provides the results.

Now, an example will be described.

Using the apparatus shown in FIG. 2A, immunoglobulin G (hereinbelow, abbreviated to "IgG") contained in human serum was measured.

An infrared emitting diode (having a maximum forward current of 200 mA, an optical output of 40 mW and a peak wavelength of 800 nm) was employed as the light source 32, and it was caused to emit light by D.C. by means of the power supply 31. The light emergent from the infrared emitting diode was made the incident light 34 through the lens unit 33, and was struck upon the sample to-be-measured 36 in the cylindrical cell made of glass 35. The scattering lights 37 and 38 from the measured sample in the directions of 35 degrees and 90 degrees with respect to the incident light 34 were respectively detected by the photo detectors 39 and 40. As the photo detectors, silicon photosensors (PN-type silicon photodiodes) were employed. The outputs of the silicon photosensors were led to the preamplifiers 41 and 42 and were amplified by the amplifiers 43 and 44, respectively. The discrimination was made with the discriminator 45. The incident light 34 and the scattering lights 37 and 38 were led through slits.

Using the above apparatus, standard curves of the IgG were obtained. 50 μl of standard IgG solutions at various concentrations were added to 5 ml of anti-human IgG serum (rabbit) diluted to 16 times. After stirring, each solution was incubated at 35° C. for 30 minutes. Each sample thus obtained was moved into the cylindrical cell of glass 35, and the light scattering intensities in the directions of 35 degrees and 90 degrees were measured. The relations between the light scattering intensities and the IgG concentration became as shown in FIG. 3. Curves 3 and 4 indicate the standard curves corresponding to the light scattering intensities in the directions of 35 degrees and 90 degrees, respectively.

Subsequently, the IgG concentration of human serum whose IgG concentration was unknown was evaluated. 50 μl of human serum diluted to 5 times was added to 5 ml of the anti-human IgG serum (diluted to 16 times, rabbit), and respective light scattering intensities in the directions of 35 degrees and 90 degrees were measured similarly to the above. The IgG concentration was determined from these light scattering intensities and the standard curves in FIG. 3.

As a result, even when the human serum contained IgG at high concentration, the IgG concentration could be quantitatively analyzed simply and accurately.

In this manner, according to this invention, even in a case of a measurement sample which contains an object to-be-measured in large amounts, the concentration of the object to-be-measured can be simply evaluated without going through the complicated procedures required in the prior art. Accordingly, the period of time required for the measurement of one sample can be shortened as compared with that in the prior-art method. A further effect is that the cost of reagents necessary for one sample is reduced.

Although the case of the measurement at two angles has been stated above, it is similarly possible to evaluate the true concentration or to detect an abnormal sample by a measurement at three or more angles. In this case, the reliability of the value obtained is naturally increased.

We claim:

1. A nephelometric immunoassay characterized in that light is projected on an unknown sample to-be-measured containing an antigen-antibody complex formed by a reaction of an antigen and an antibody solution, that at least two light scattering intensities at different angles with respect to the incident light are measured, and that a true antigen concentration is discriminated using only a single sample concentration of said unknown sample from plural antigen concentration values which are obtained from the measurement of each light scattering intensity from said single sample concentration by comparing said plural antigen concentration values, wherein the discrimination of the true antigen concentration is determined by numerically determining whether $|\ln Cx\alpha - \ln Cx\beta|$ is less than $|\ln C'x\alpha - \ln C'x\beta|$, wherein $Cx\alpha$ and $C'x\alpha$ denote values of antigen concentrations for light scattering intensity of one angle and $Cx\beta$ and $C'x\beta$ denote values of antigen concentrations for light scattering intensity of another angle.

2. A nephelometric immunoassay as defined in claim 1, wherein the different angles are angles which differ at least 5 degrees.

3. A nephelometric immunoassay as defined in claim 1, wherein one of the scattering lights is a scattering light which is at an angle selected from a range of 30 to 45 degrees with respect to said incident light, while the other scattering light is a scattering light which is at an angle selected from a range of 80 to 100 degrees with respect to said incident light.

4. A nephelometric immunoassay as defined in claim 1, wherein the measurement of said light scattering intensities is a measurement which simultaneously assesses said light scattering intensities with two photo detectors.

5. A nephelometric immunoassay characterized in that light is projected on a sample to-be-measured containing an antigen-antibody complex formed by a reaction of an antigen and an antibody solution, that at least two light scattering intensities at different angles with respect to the incident light are measured, and that a true antigen concentration is discriminated from plural antigen concentration values which are obtained from the measurement of each light scattering intensity by comparing said plural antigen concentration values, wherein the discrimination of the true antigen concentration is determined by numerically comparing $|\ln Cx\alpha - \ln Cx\beta|$, $|\ln C'x\alpha - \ln C'x\beta|$, $|\ln Cx\alpha - \ln C'x\beta|$ and $|\ln C'x\alpha - \ln Cx\beta|$, wherein $Cx\alpha$ and $C'x\alpha$ denote values of antigen concentrations for light scattering intensity of one angle and $Cx\beta$ and $C'x\beta$ denote values of antigen concentrations for light scattering intensity of another angle.

6. A nephelometric immunoassay as defined in claim 5, wherein the different angles are angles which differ at least 5 degrees.

7. A nephelometric immunoassay characterized in that light is projected on a sample to-be-measured containing an antigen-antibody complex formed by a reaction of an antigen and an antibody solution, that at least two light scattering intensities at different angles with respect to the incident light are measured, and that a true antigen concentration is discriminated from plural antigen concentration values which are obtained from the measurement of each light scattering intensity by comparing said plural antigen concentration values, wherein the discrimination of the true antigen concentration is determined by numerically comparing $|Cx\alpha - Cx\beta|/Cx\alpha$ or $|Cx\beta - Cx\alpha|/Cx\beta$ and a, wherein $Cx\alpha$ denotes a value of antigen concentration in a range which does not include the range of antigen excess for light scattering intensity of one angle, and $Cx\beta$ denotes a value of antigen concentration in the range which does not include the range of antigen excess for light scattering intensity of another angle, and a is a value which is to be empirically set.

8. A nephelometric immunoassay as defined in claim 7, wherein the different angles are angles which differ at least 5 degrees.

9. A nephelometer for immunoassay comprising:
means for projecting light on an unknown sample to-be-measured containing an antigen-antibody complex formed by a reaction of an antigen and an antibody solution;
means for measuring at least two light scattering intensities at different angles with respect to the incident light; and
means for discriminating a true antigen concentration using only a single sample concentration of said unknown sample from plural antigen concentration values which are obtained from the measurement of each light scattering intensity from said single sample concentration by comparing said plural antigen concentration values, wherein the discrimination of the true antigen concentration is determined by numerically determining whether $|\ln Cx\alpha - \ln Cx\beta|$ is less than $|\ln C'x\alpha - \ln C'x\beta|$, whwerein $Cx\alpha$ and $C'x\alpha$ denote values of antigen concentrations for light scattering intensity of one angle and $Cx\beta$ and $C'x\beta$ denote values of antigen concentrations for light scattering intensity of another angle.

10. A nephelometer as defined in claim 9, wherein the light scattering intensity measuring means comprises two photo detectors which are disposed at angles differing at least 5 degrees with respect to said incident light.

11. A nephelometer as defined in claim 10, wherein one of said two photo detectors is disposed at a position at which it detects scattering light at an angle selected from a range of 30 to 45 degrees with respect to said incident light, while the other photo detector is disposed at a position at which it detects scattering light at an angle selected from a range of 80 to 100 degrees with respect to said incident light.

12. A nephelometer as defined in claim 9, wherein the light scattering intensity measuring means comprises a single photo detector, wherein the position of the photo detector is moved in order to detect said light scattering intensities at different angles.

13. A nephelometer as defined in claim 9, wherein the light scattering intensity measuring means comprises a single photo detector, wherein said light scattering intensities at different angles are successively led to said photo detector by optical guides.

14. A nephelometer for immunoassay comprising:
means for projecting light on a sample to-be-measured containing an antigen-antibody complex formed by a reaction of an antigen and an antibody solution;
means for measuring at least two light scattering intensities at different angles with respect to the incident light; and
means for discriminating a true antigen concentration from plural antigen concentration values which are obtained from the measurement of each light scattering intensity by comparing said plural antigen concentration values, wherein the discrimination of the true antigen concentration is determined by numerically comparing $|\ln Cx\alpha - \ln Cx\beta|$, $|\ln C'x\alpha - \ln C'x\beta|$, $|\ln Cx\alpha - \ln C'x\beta|$ and $|\ln C'x\alpha - \ln Cx\beta|$, wherein $Cx\alpha$ and $C'x\alpha$ denote values of antigen concentrations for light scattering intensity of one angle and $Cx\beta$ and $C'x\beta$ denote values of antigen concentrations for light scattering intensity of another angle.

15. A nephelometer as defined in claim 14, wherein the light scattering intensity measuring means comprises two photo detectors which are disposed at angles differing at least 5 degrees with respect to said incident light.

16. A nephelometer for immunoassay comprising:
means for projecting light on a sample to-be-measured containing an antigen-antibody complex formed by a reaction of an antigen and an antibody solution;
means for measuring at least two light scattering intensities at different angles with resepect to the incident light; and
means for discriminating a true antigen concentration from plural antigen concentration values which are obtained from the measurement of each light scattering intensity by comparing said plural antigen concentration values, wherein the discrimination of the true antigen concentration is determined by numerically comparing $|C_{x\alpha} - C_{x\beta}|/C_{x\alpha}$ or $|C_{x\beta} - C_{x\alpha}|/C_{x\beta}$ and a, wherein $C_{x\alpha}$ denotes a value of antigen concentration in a range which does not include the range of antigen excess for light scattering intensity of one angle, and $C_{x\beta}$ denotes a value of antigen concentration in the range which does not include the range of antigen excess for light scattering intensity of another angle, and a is a value which is to be empirically set.

17. A nephelometer as defined in claim 16, wherein the light scattering intensity measuring means comprises two photo detectors which are disposed at angles differing at least 5 degrees with respect to said incident light.

* * * * *